(12) United States Patent
Wegener et al.

(10) Patent No.: US 10,926,895 B2
(45) Date of Patent: Feb. 23, 2021

(54) METHODS AND SYSTEMS FOR CONTROLLING THE FLOW RATE IN A PNEUMATIC SYRINGE

(71) Applicant: Fenwal, Inc., Lake Zurich, IL (US)

(72) Inventors: Christopher J. Wegener, Libertyville, IL (US); Robert Ciechowski, Evanston, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 16/682,173

(22) Filed: Nov. 13, 2019

(65) Prior Publication Data

US 2020/0198814 A1    Jun. 25, 2020

Related U.S. Application Data (60) Provisional application No. 62/781,789, filed on Dec. 19, 2018.

(51) Int. Cl.
*A61M 5/31* (2006.01)
*B65B 3/00* (2006.01)

(52) U.S. Cl.
CPC .............. *B65B 3/003* (2013.01); *A61M 5/31* (2013.01); *A61M 2005/3114* (2013.01); *A61M 2205/3331* (2013.01); *A61M 2209/045* (2013.01)

(58) Field of Classification Search
CPC . B65B 3/003; A61M 5/31; A61M 2005/3114; A61M 2205/3331; A61M 2209/045; A61M 5/1456; A61M 5/155; A61M 5/145
See application file for complete search history.

(56) References Cited

U.S. PATENT DOCUMENTS

| 2017/0204371 A1 | 7/2017 | Wegener |
| 2020/0046899 A1* | 2/2020 | Cane' ................. A61M 5/3148 |

FOREIGN PATENT DOCUMENTS

| WO | WO01/21234 A1 | 3/2001 |
| WO | WO2018/065880 A1 | 4/2018 |

OTHER PUBLICATIONS

European Patent Office, Extended European Search Report, counterpart EP Appl. No. 19210245, dated May 7, 2020 (7 pages).

* cited by examiner

*Primary Examiner* — Jason K Niesz
(74) *Attorney, Agent, or Firm* — Cook Alex Ltd.

(57) ABSTRACT

A method for controlling the flow rate of a pneumatic syringe in a system that includes a disposable fluid circuit and reusable hardware configured to accept the disposable fluid circuit. The disposable fluid circuit includes one or more syringes, while the reusable hardware includes a syringe pump for each syringe of the disposable fluid circuit and a controller. The syringe pump includes a vacuum/pressure source for moving the piston within the syringe and a position detector for indicating the position of the piston within the syringe. The method controls several distinct phases of the process: break pressure targeting, glide control and vent control, and the method is the same regardless of whether a positive pressure or a vacuum is applied to the piston of the syringe. Preferably, a proportional-integral-derivative ("PID") feedback loop is used for controlling the movement of the piston in the syringe.

9 Claims, 12 Drawing Sheets

METHODS AND SYSTEMS FOR CONTROLLING THE FLOW RATE IN A PNEUMATIC SYRINGE

TECHNICAL FIELD

The present disclosure is generally directed to systems and methods for processing small volumes of suspensions of cells, and then filling the cell suspension into one or more containers. More particularly, the present disclosure is directed to systems and methods for controlling the flow rate of a pneumatic syringe used in the processing small of volumes of cells.

BACKGROUND

A number of well-known therapies are currently practiced in which a targeted cellular blood component (e.g., red blood cells, white blood cells, and platelets) is separated from whole blood and stored for later infusion to a patient. The targeted cell product (e.g., red blood cells or platelets) may be in a suspension that includes plasma and/or some other supernatant. As such, it is sometimes desirable to "wash" the cellular suspension (typically with saline) to remove the plasma/supernatant, as well as any non-target cellular material, prior to reinfusion.

There are instances in which small final volumes (e.g., 10 mL) are desired, such as when processing single-dose quantities of mononuclear cell products. Thus, systems and methods for processing small volumes of cellular suspensions have been provided. See, e.g., US 2017/0204371, which is incorporated herein by reference. Such a machine and fluid circuit for processing small volumes of cell suspension can be configured and operated to further direct these small volumes directly into one or more small volume delivery containers without the need to use an intermediate large volume container for storage, as shown and described in U.S. Provisional Pat. Appln. Ser. No. 62/672,236, filed May 16, 2018, which is also incorporated herein by reference.

SUMMARY

In a first aspect, a method is provided for controlling movement of a piston in a syringe with a system comprising a pump for introducing pressurized air/vacuum into the syringe to act on a first side of the piston and a programmable controller for automatically operating the system. The method comprises a first step of operating the pump at a first speed to introduce pressurized air/vacuum into the syringe to act on the first side of the piston, after which the following steps are performed: decreasing the speed of the pump linearly to -0- until a nominal break pressure is achieved; increasing the pump speed until movement of the piston is detected; determining a target volume $V_{target}$ for the syringe for each increment of time after movement of the piston has been detected based on a target flow rate; measuring a current volume $V_{current}$ of the syringe at each time increment; determining a volumetric error $V_{error}$ at each increment of time, such that $V_{error}=V_{target}-V_{current}$; determining a controller output based on $V_{error}$ using Proportional-Integral-Derivative control logic; adjusting the pump speed according to the controller output; establishing a vent volume $V_{vent}$ as a multiple of $V_{target}$ for each time increment; at each increment of time, if $V_{current}>V_{vent}$, releasing pressure/vacuum from the first side of the piston until $V_{current}<V_{vent}$; and if movement of the piston has stopped, returning to the first step of the method without resetting $V_{target}$.

In a further aspect of the method, if $V_{error}<$-0-, increasing the pump speed, and If $V_{error}>$-0-, stopping the pump.

In a further aspect of the method, the time duration for releasing the pressure/vacuum is constant. Alternatively, the time duration for releasing the pressure/vacuum is variable. If the time duration is variable, then the time duration for releasing the pressure/vacuum preferably is a function of the magnitude of $V_{error}$.

In an additional aspect, the method further comprises resetting the target flow rate and resetting $V_{target}$ for the syringe for each increment of time after movement of the piston has been detected based on the reset target flow rate.

In an additional aspect, the method further comprises determining the nominal break pressure empirically for multiple syringes and is set so that the nominal break pressure is obtained before movement of the piston is detected.

In a further aspect of the method, once the pump is operated at the first speed, the speed of the pump is decreased linearly to -0-.

In another aspect, a system for controlling movement of a piston in a syringe with air pressure/vacuum is provided that comprises a pump for introducing pressurized air/vacuum into the syringe to act on the first side of the piston; a sensor for determining the pressure/vacuum acting on the first side of the piston; a vent for selectively releasing the pressurized air/vacuum acting on the first side of the piston; sensors for determining a location of the piston within the syringe and a volume of a space defined by syringe and the second side of the piston; and a controller configured to operate the system to perform the method of any of aspects described above.

DETAILED DESCRIPTION

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Figure 1:
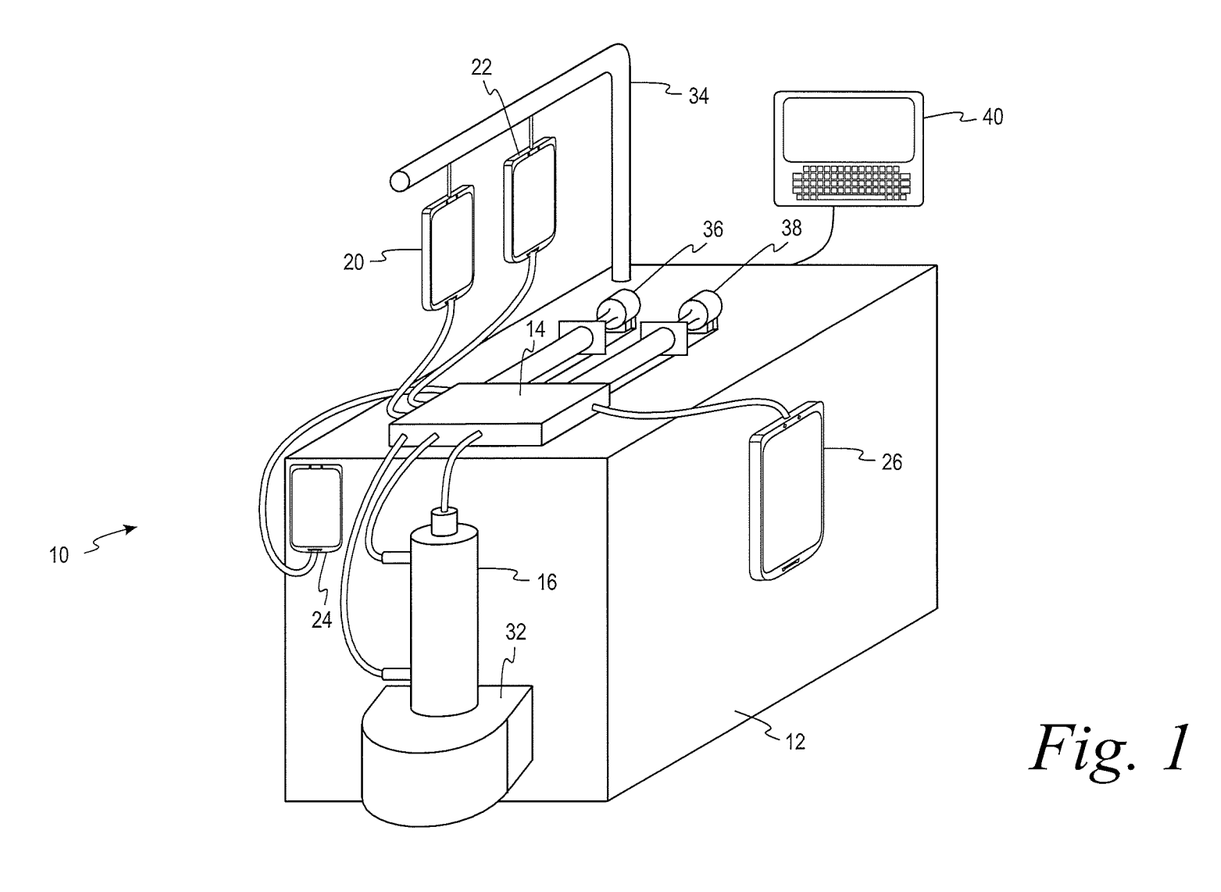
FIG. 1 is a perspective view of a system for processing (e.g., washing) small volumes of cellular suspensions including a reusable machine and a disposable fluid circuit, or kit.

Turning first to FIG. 1, an embodiment of a system 10 for processing cell suspensions (e.g., cell washing) is illustrated, the system 10 including a reusable hardware component 12 and a disposable kit component (also referred to as a fluid circuit or set) 14.

Figure 2:
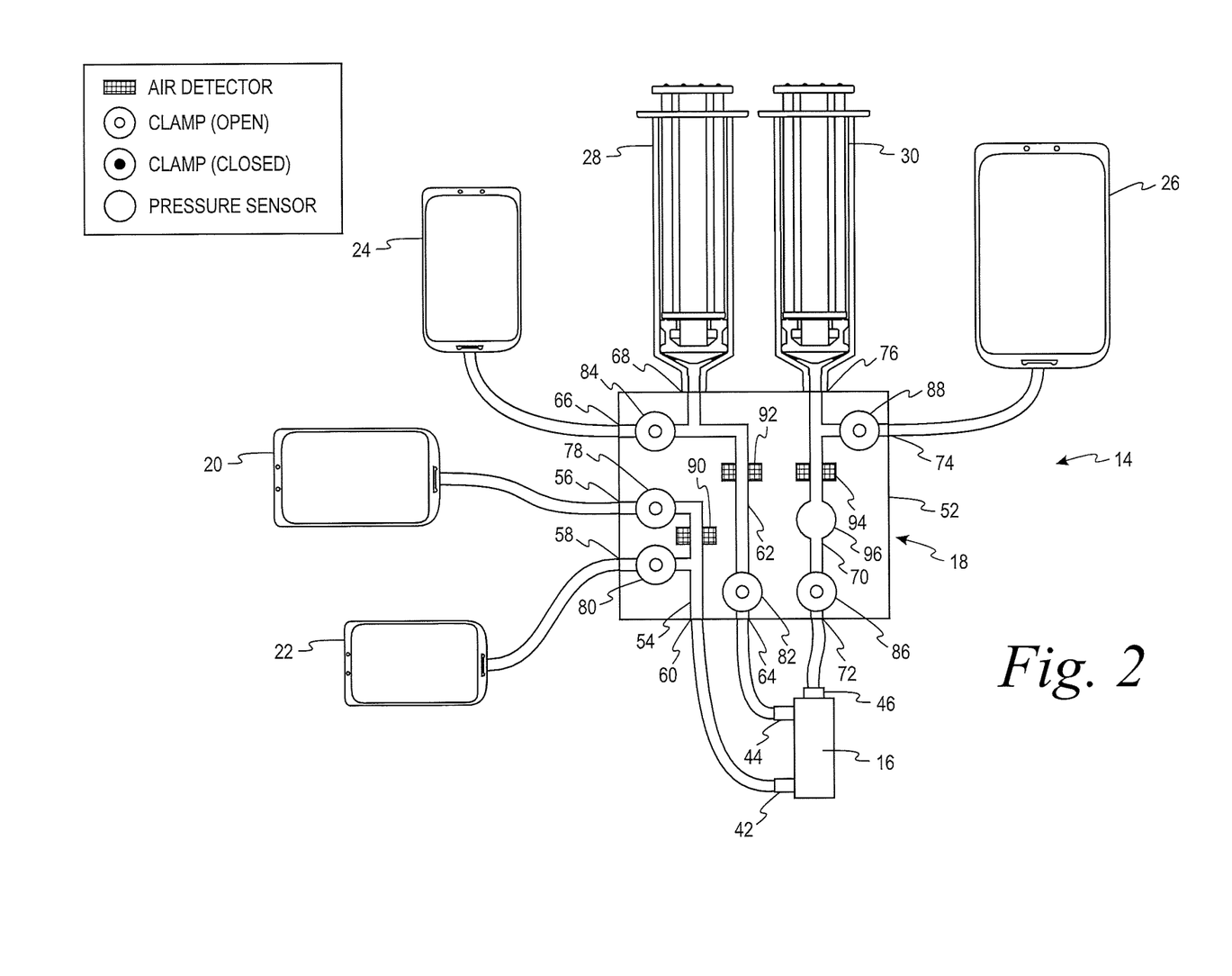
FIG. 2 is a schematic view of the disposable kit for use in the system of FIG. 1.

As seen in FIG. 2, the disposable kit 14 includes a spinning membrane separator 16 (such as is well known in the art), a cassette 18 for providing fluid management through the kit, and various containers 20, 22, 24, 26 and syringes 28, 30 (each comprising a body or barrel portion and a plunger) in fluid communication with the cassette 18. Tubings interconnect each of the various containers 20, 22, 24, 26, as well as the inlet and outlets of the spinning membrane separator 16, to the cassette 18.

Returning to FIG. 1, the reusable hardware component 12 includes a drive system/support 32 for the spinning membrane separator 16, supports 34 for the various containers of the disposable kit, a syringe pump 36, 38 for each syringe 28, 30, and a controller 40 programmed for automatically controlling operation of the system. The controller 40 may include a microprocessor (which, in fact may include multiple physical and/or virtual processors). According to other embodiments, the controller 40 may include one or more electrical circuits designed to carry out the actions described herein. In fact, the controller 40 may include a microprocessor and other circuits or circuitry. In addition, the controller 40 may include one or more memories. The instructions by which the microprocessor is programmed may be stored on the one or more memories associated with the microprocessor, which memory/memories may include one or more tangible non-transitory computer readable memories, having computer executable instructions stored thereon, which when executed by the microprocessor, may cause the microprocessors to carry out one or more actions as described below.

Specifically, the disposable kit 14 comprises a spinning membrane separator 16 having an inlet 42 for flowing the suspension of cellular material to be washed and a wash medium into the spinning membrane separator, a first outlet 44 for flowing retentate comprising washed cells from the spinning membrane separator, and a second outlet 46 for flowing filtrate comprising a non-cellular component of the cellular suspension and wash medium from the spinning membrane separator.

The kit further includes containers 24, 26 for receiving the retentate and the filtrate, respectively, and also either includes a container 22 of wash medium integrally connected to the kit at the time of manufacture or is configured to be connected to a container of wash medium at the point of use.

Fluid management of the kit 14 is controlled by the cassette 18, which cassette 18 may also be referred to as a fluid management system. The cassette 18 comprises a housing 52 having a series of fluid pathways therein interconnecting the various other components of the disposable kit 14, each of the fluid pathways having flow control mechanisms associated therewith that are automatically operated by the controller 40, which flow control mechanisms may include valves and air detectors/pressure sensors.

Devices for selectively occluding the fluid pathways are associated with various of the fluid pathways in the cassette. Such occluding devices may take the form of valves or clamps, and according to one embodiment may take the form of pinch valves. For ease of explanation, the devices for selectively occluding the fluid pathways, irrespective of their structure, will be referred to as valves. As shown in FIG. 2, the cassette includes valves 78, 80, 82, 84, 86 and 88.

Various of the fluid pathways may also be provided with a sensor, such as sensors 90, 92, 94, that are able to detect differences in the fluid passing through the fluid pathways. Specifically, the sensors 90, 92, 94 are able to detect interfaces between different types of fluids, such as an air-liquid interface, a wash media-retentate interface, and a wash media-filtrate interface. Upon the detection of such interfaces, a signal is sent to the controller 40 that will act to control the configuration of the valves (open or closed) and actuate the syringe pumps 36, 38 to move fluid through the kit 14 in accordance with a cell washing procedure. The cassette 18 may also include a pressure sensor 96 for monitoring purposes.

A cell washing procedure utilizing the system 10 generally includes three relatively distinct phases: a priming phase, during which the kit 14 is primed with wash media; a loading phase, in which the annulus of the spinning membrane separator 16 is filled with the cellular suspension that is to be washed; and a wash phase, in which retentate (the washed cells) and filtrate (supernatant and wash media) are drawn through the cassette and flowed to their respective containers.

As is appreciated, the procedure may be automatically controlled by the programmable controller 40, which sequentially operates the valves 78, 80, 82, 84, 86, 88 and the syringe pumps 36, 38, in accordance with signals received from the sensors 90, 92, 94, 96.

Because such small volumes are being processed by the system described above, a mechanism is provided for filling the cell product processed using the system 10 directly into low-volume containers (e.g., between 1 mL and 50 mL), such as may be used to administer the cell product. For example, such a low-volume container may be a syringe may also serve as a delivery container (e.g., for administration to a patient), and may also be a single-use delivery container (e.g., for administration to a patient with disposal of the container thereafter).

Figure 3:
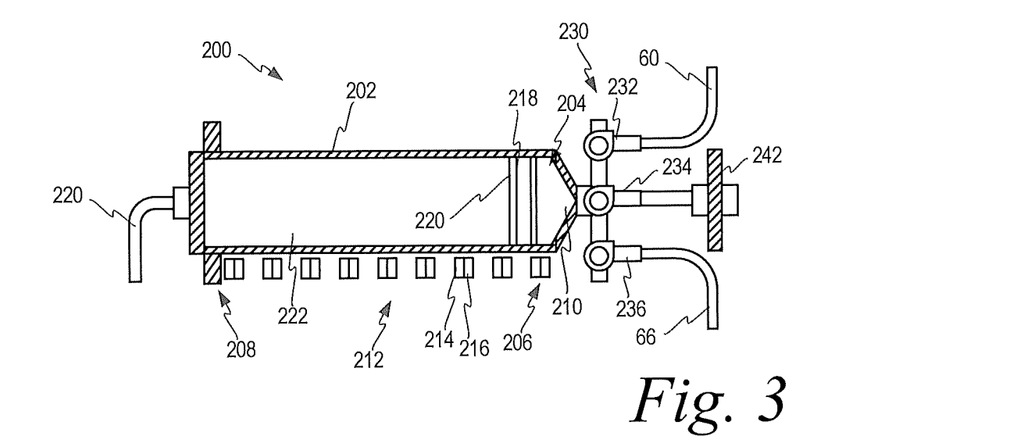
FIG. 3 is a cross-sectional view of an embodiment of a syringe/syringe pump as may be used as part of the system of FIGS. 1 and 2, with a plunger head assembly in a first position.
Figure 4:
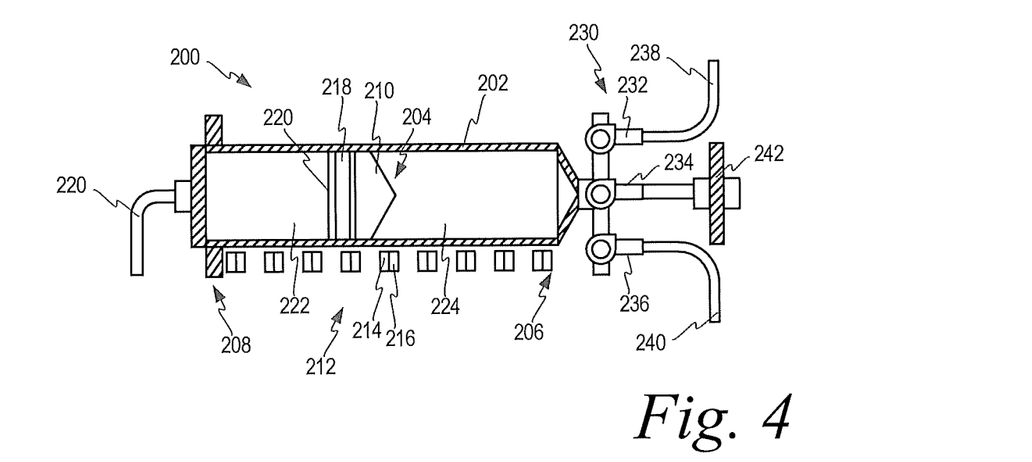
FIG. 4 is a cross-sectional view of the syringe/syringe pump of FIG. 3, with a plunger head assembly in a second position.
Figure 5:
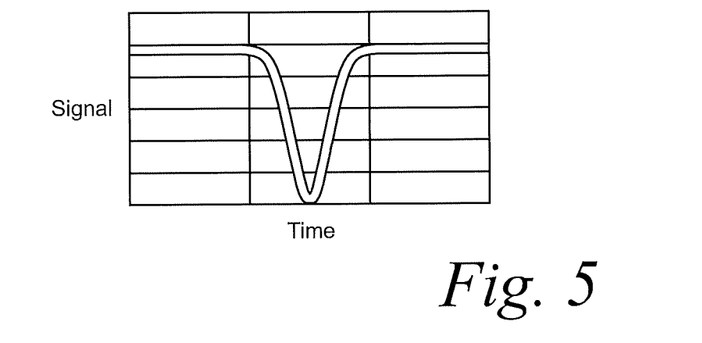
FIG. 5 is a chart of the signal response of one of the infrared detectors or sensors of the syringe/syringe pump of FIG. 4.

When filling such low-volume containers, it is important to provide controlled delivery of the cell product or solution to the connected containers. FIGS. 3 and 4 illustrate an embodiment of a syringe/syringe pump 200 that may be used to fill low-volume containers, which syringe/syringe pump 200 may be substituted for the syringe 28 and syringe pump 36, for example, or may be used in conjunction with the system 10 in place of the container 24. FIGS. 6-12 illustrate another embodiment of a syringe/syringe pump 300 that may be used to fill low-volume containers, specifically the syringe component of the syringe/syringe pump 300. This syringe/syringe pump 300 may be used in place of the syringe 28 and syringe pump 36, or may be used in conjunction with the system 10 in place of the container 24. For ease of explanation, the combination of syringe and syringe pump 200, 300 shall be referred to simply as syringe pump 200, 300 herein.

It will be recognized that aspects of the syringe pumps 200, 300 may be advantageously incorporated into the system 10, even if the syringe pumps 200, 300 are not used for filling low-volume containers (e.g., syringes). For example, the filtered pneumatic system used to move the piston or plunger head back and forth along the length of the barrel may be used with the remainder of the system 10 as described above, even if the syringe pump is not used to fill low-volume containers.

Turning first to the embodiment of the syringe pump 200 illustrated in FIGS. 3 and 4, the syringe pump 200 includes a syringe barrel 202 (which may be made of polypropylene, cyclic olefin copolymer, or other materials such as may be inert, optically clear and, for certain applications, liquid-nitrogen compatible) and a piston or plunger head assembly 204. The plunger head assembly 204 is moveable (translatable) between a first end 206 and a second end 208 of the barrel 202.

The plunger head assembly 204 includes the plunger 210 and one part of a position detector 212. According to the illustrated embodiment, the position detector 212 also includes a plurality of transmitter/sensor pairs 214, 216. According to the illustrated embodiment, the transmitters (or emitters) 214 may be in the form of infrared light emitting diodes, and the sensors 216 may be in the form of infrared sensors. According to other embodiments, the transmitters and sensors may use visible or ultraviolet light, capacitance, or magnetic forces, for example. The transmitter/sensor pairs 214, 216 are disposed along the length of the barrel 202 between the first end 206 and the second end 208. The pairs 214, 216 operate in conjunction with an infrared reflector 218 that is part of the plunger head assembly 204. As one example, the reflector 218 may be in the form of a reflective strip that is disposed about the perimeter of a rigid disc 220 that is attached opposite the plunger 210.

In operation, the position detector 212 (which could be coupled to the controller 40, for example) would use the interaction between the transmitter/sensor pairs 214, 216 and the reflector 218 to determine the position of the plunger head assembly 204 along the barrel 202. In particular, light emitted from the transmitter 214 would be received by the sensor 216 (or would be received over a threshold amount) if the light contacts the reflector 218. Otherwise, the light would not be received by the sensor 216 (or would not be received below the threshold amount). Depending on the amount of light received by the sensor 216, a signal generated by the sensor 216 would vary. Depending on the signals received from the individual transmitter/sensor pairs 214, 216, the controller 40 may determine the position of the plunger head assembly 204 along the barrel 202 between the first and second ends 206, 208.

A vacuum/pressure source (e.g., a diaphragm pump) is attached via line (e.g., tubing) 220 to the end 208 of the barrel 202. The end 208 is otherwise closed, forming a first variable volume space 222 between the closed end 208 of the barrel 202 and the plunger head assembly 204. Filtered air may be pumped into and out of the space 222 to cause the plunger head assembly 204 to move between the first and second ends 206, 208 of the barrel 202.

According to embodiments where the syringe pump 200 is used in conjunction with the system 10, the vacuum/pressure source instead may permit the plunger head assembly 204 to move in response to the action of the syringe 28/syringe pump 36 pushing fluid into the barrel 202, by venting the space 222, for example. The movement of the plunger head assembly 204 causes a second variable volume space 224 to open between the plunger head assembly 204 and the first end 206 to receive fluid (e.g., a cell product) into the barrel 202. Compare FIGS. 3 and 4. Fluid may be drawn into (or may enter into) and ejected or delivered from the space 224 according to the movement of the plunger head assembly 204.

A set 230 of as many as three valves 232, 234, 236 is attached to the end 206 of the barrel 202. The set of valves 230 may be coupled to the controller 40 (potentially via other equipment, such as motors); the set 230 may be coupled as a group, or as individual valves 232, 234, 236. According to one use of the syringe pump 200, the syringe pump 200 may take the place of the syringe 28 and syringe pump 36 of the system 10 as explained above. As such, the valves 232, 236 may correspond to the valves 82, 84, and valves 232 may connect the barrel 202 to the spinning membrane 16 via the fluid pathway 62, and to a low-volume container via the outlet 66. While the valves 232, 236 may appear as stopcocks in the illustration of 3, the structures (e.g., pinch valves) defining valves 82, 84 discussed above may be used in the place of the illustrated stopcocks. The valve 234 connects the barrel 202 to a filtered vent 242 to permit the barrel 202 to vent to atmosphere, for example, and it too may be incorporated into the embodiment of the system 10 as illustrated in FIGS. 1 and 2.

In operation, the plunger head assembly 204 starts at a first position, such as is illustrated in FIG. 3. The controller 40 opens the valve 232 and causes the vacuum/pressure source to operate, and draw vacuum behind the plunger head assembly 204 (i.e., space 222). As a consequence, the plunger head assembly 204 moves in the direction of the end 208 (i.e., from the end 206 to the end 208) and draws fluid from the annulus of the spinning membrane 16 via the second fluid pathway 62 into the space 224 (see FIG. 4).

The controller 40 may subsequently close valve 232, open valve 236 and operate the vacuum/pressure source to pump pressurized air into the space 222. This causes the plunger head assembly 204 to move in the direction of the end 206 (i.e., from the end 208 to the end 206) and push fluid to the low-volume container via the outlet 66 from the space 224. The low-volume container may be a syringe, for example, with the outlet 66 in fluid communication with the barrel of the syringe via a tip of the syringe, for example.

To limit the fluid remaining in the barrel 202, the controller 40 may close the valve 236, open the valve 234 and cause the vacuum/pressure source to operate to draw vacuum behind the plunger head assembly 204. As a consequence, air is drawn through the filtered vent 242 into the space 224. The controller 40 then closes the valve 234, opens the valve 236, and causes the vacuum pressure source to operate to pump pressurized air into the space 222. This causes the plunger head assembly 204 to again move in the direction of the end 206 and push any remaining fluid to the container (e.g., syringe) via the outlet 66. Any remaining air may be subsequently exhausted through the vent 242.

The pneumatic control of filtered air in and out of the space 222 provides certain advantages over the use of a syringe with a plunger arm where one end of the barrel remains open to the surrounding environment. By leaving the barrel end open, materials could collect on an inner surface of the barrel wall, such that movement of the plunger head between the ends could permit the materials on the inner surface to interact with the fluid on the other (i.e., wet-side) of the plunger head. The use of filtered air in the space 222 to move the plunger 210 reduces or eliminates this potential source of contaminants. Further, the position detector 212 permits very precise control of the operation of the syringe pump 200. Because these advantages are not limited to the use of the syringe pump 200 (in whole or in part) in place of the syringe 28 and pump 36 in the system 10 to fill low-volume containers, the syringe pump 200 may also be used (in whole or in part) in place of the syringe 30 and pump 38, with the valves 232, 236 corresponding to the valves 86, 88.

As an alternative to replacement of syringe 28/syringe pump 36 and/or syringe 30/syringe pump 38, the syringe pump 200 may be connected to the system 10 illustrated in FIGS. 1 and 2 in place of the container 24. For example, the valve 232 may be coupled, so as to be permanently attached to or to be removably detachable from the outlet 66. One or more containers may then be detachably coupled to the valve 236, the operation of the syringe pump 200 causing the one or more containers to be filled with a cell product obtained from the system 10.

According to such an embodiment, the syringe pump 200 may be coupled to and operated by the controller 40, or the syringe pump 200 may be coupled to and operated by separate controller. The separate controller, like the controller 40, may include a microprocessor (which, in fact may include multiple physical and/or virtual processors). According to other embodiments, the separate controller may include one or more electrical circuits designed to carry out the actions described herein. The separate controller may include a microprocessor and other circuits or circuitry. In addition, the separate controller may include one or more memories. The instructions by which the microprocessor is programmed may be stored on the one or more memories associated with the microprocessor, which memory/memories may include one or more tangible non-transitory computer readable memories, having computer executable instructions stored thereon, which when executed by the microprocessor, may cause the microprocessors to carry out one or more actions as described above relative to the syringe pump 200.

Another embodiment of a syringe/syringe pump 300 that may be incorporated into or used in conjunction with the system 10 is illustrated in FIGS. 6-14. According to this embodiment, one or more syringes are filled directly and then detached from the syringe pump 300, which syringes may be intended for storage, shipment, and ultimately use. Thus, these syringes may be delivery containers, and specifically single-use containers. The syringes also may be referred to as pre-filled syringes, in that there is no need to fill the syringes from another container at the time of use.

Figure 6:
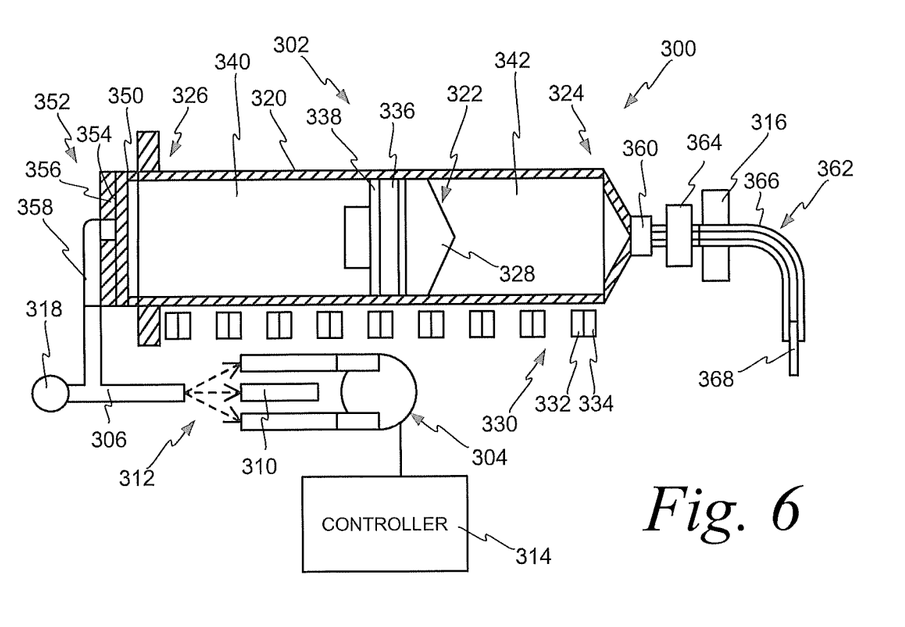
FIG. 6 is a partial schematic diagram of another embodiment of a syringe/syringe pump for producing a pre-filled syringe, which embodiment may be used with a product container such as may be produced in accordance with the embodiment of FIGS. 1-2.
Figure 7:
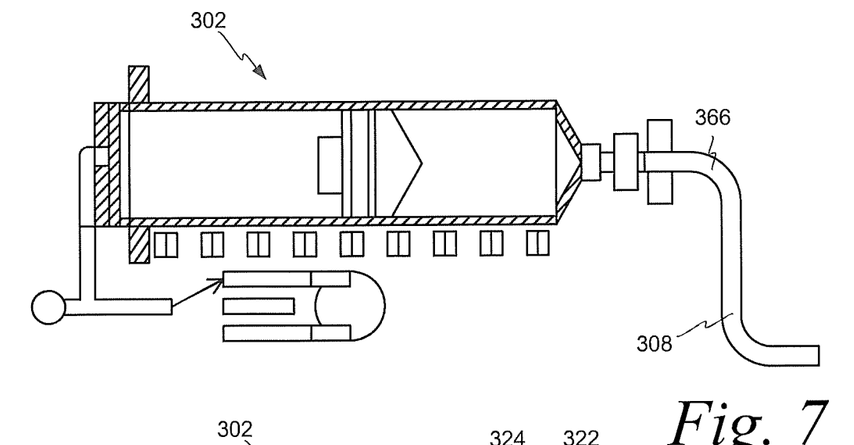
FIGS. 7-12 are partial schematic diagrams of different operational states or positions of the embodiment of FIG. 6.

FIG. 6 illustrates the combination of syringe/syringe pump 300 (referred to simply as syringe pump 300 for ease of explanation). The syringe pump 300 includes a syringe 302, a vacuum/pressure pump 304, a line (e.g. tubing) 306 that connects the pump 304 to one end of the syringe 302, a line (e.g. tubing) 308 (see FIG. 7) that connects the syringe 302 to the system 10 for example, a vent 310, and a valve assembly 312 (which may include one or more valves) to selectively connect the line 306 to the pump 304 and the vent 310.

The filling system 300 also includes a controller 314 (which may be the controller 40 according to certain embodiments, and to which the comments made above relative to controller 40 may also apply), which controller 314 is coupled to the pump 304 and may be coupled to other elements as well. For example, the controller may be coupled to the valve assembly 312, a sensor 316 (for example an air or fluid sensor), and a sensor 318 (for example a pressure sensor to sense the driving pressure/vacuum applied by the pump 304 and to provide feedback to the controller 314). The pump 304 and the controller 314 may be associated with a plurality of syringes 302, of which one is illustrated in FIGS. 6-12. While the syringe 302 is illustrated as horizontal in FIGS. 6-12, the syringe 302 may be vertically oriented in actual operation of the system 300, as noted below.

The syringe 302 includes a syringe barrel 320 (which may be made of polypropylene, cyclic olefin copolymer, or other materials such as may be inert, optically clear and, for certain applications, liquid-nitrogen compatible) and a piston or plunger head assembly 322. The plunger head assembly 322 is moveable (translatable) between a first end 324 of the barrel 320 and a second end 326 of the barrel 320. The plunger head assembly 322 includes the plunger 328 and one part of a position detector 330.

According to the illustrated embodiment, the position detector 330 also includes a plurality of transmitter/sensor pairs 332, 334. The transmitters (or emitters) 332 may be in the form of infrared light emitting diodes, and the sensors 334 may be in the form of infrared sensors. The transmitter/sensor pairs 332, 334 are disposed along the length of the barrel 322 between the first end 324 and the second end 326. The pairs 332, 334 operate in conjunction with an infrared reflector 336 that is part of the plunger head assembly 322. As one example, the reflector 336 may be in the form of a reflective strip that is disposed about the perimeter of a rigid disc 338 that is attached opposite the plunger 328. The disc 338 may also assist in maintaining the coaxial alignment of the plunger assembly 322 within the barrel 320.

In operation, the position detector 330 (coupled to the controller 314) would use the interaction between the transmitter/sensor pairs 332, 334 and the reflector 336 to determine the position of the plunger head assembly 322 along the barrel 320. In particular, light emitted from the transmitter 332 would be received by the sensor 334 (or would be received over a threshold amount) if the light contacts the reflector 336. Otherwise, the light would not be received by the sensor 334 (or would not be received below the threshold amount). Depending on the amount of light received by the sensor 334, a signal generated by the sensor 334 would vary. Based on the signals received from the individual transmitter/sensor pairs 332, 334, the controller 314 may determine the position of the plunger head assembly 322 along the barrel 320 between the first and second ends 324, 326.

As described above, the pump 304 is attached via line 306 to the syringe 302, and more particularly to the end 326 of the barrel 320. The end 326 is otherwise closed, forming a first variable volume space 340 between the closed end 326 of the barrel 320 and the plunger head assembly 322. Filtered air may be pumped into and out of the space 340 to move the plunger head assembly 322 between the first and second ends 324, 326 of the barrel 320. According to embodiments where the syringe pump 300 is used in conjunction with the system 10, the vacuum/pressure source instead may permit the plunger head assembly 322 to move in response to the action of the syringe 28/syringe pump 36 pushing fluid into the barrel 320, by venting the space 340, for example. The movement of the plunger head assembly 322 causes a second variable volume space 342 to open between the plunger head assembly 322 and the first end 324 and the first end 324 to receive fluid (e.g., a cell product) into the barrel 320. Fluid may be drawn into (or may enter into) the space 342 according to the movement of the plunger head assembly 322.

The syringe 302 may include an aperture 350 at the second end 326, and a filter assembly 352 may include a first connector 354 that permits the filter assembly 352 to be connected to the second end 326 in the aperture 350. According to one embodiment, the first connector 354 may be an O-ring that is received within the aperture 350 to connect the filter assembly 352 to the syringe 302. According to other embodiments, the aperture 350 may be threaded on an inner surface, the first connector 354 may be similarly threaded on an outer surface, and the threaded surfaces may mate to connect the filter assembly 352 to the syringe 302. The filter assembly 352 may also include a filter 356 and a second connector 358 for connection with the line 306. The filter 356 may be a 0.2 µm polytetrafluoroethylene (PTFE) hydrophobic sterile filter. According to one embodiment, the second connector 358 may include an O-ring disposed within a passage, the O-ring receiving an end of the line 306 therethrough to connect the filter assembly 352 to the line 306. According to other embodiments, the second connector 358 may be a female luer slip, for example. The filter assembly 352 closes the end 326 of the barrel 320 and filters the air passing into the space 340.

The syringe 302 may also include a male luer-lock tip 360. Attached to the tip 360 is an assembly 362 that permits the syringe 302 to be connected to a fluid pathway, for example. The assembly 362 includes a female luer-lock connector 364 that may be connected to the male luer-lock tip 360, a section of weldable tubing 366 connected at a first end to the connector 364, and a sealing plug 368 received within a second end of the weldable tubing 366.

In operation, the system 300 may perform an integrity check on the syringe as illustrated in FIG. 6. The controller 314 operates the pump 304 to pump pressurized air into space 340. The controller 314 determines if the position detector 330 indicates that the position of the plunger head assembly 322 has moved. The controller 314 may also determine if other sensors, such as a pressure sensor, indicate that the pressure of the air in the space 340 has changed. If the controller 314 determines that the plunger head assembly 322 has not moved and that the pressure in the space 340 has not changed, the system 300 may begin a method to fill the syringe 302.

Preferably, the syringe is pre-connected to the tubing set at the time of manufacture. Alternatively, the syringe may be connected to the tubing 366 of the tubing set by, e.g., sterile welding tubing 308, 366. See FIG. 7. The controller 314 then operates the pump 304 to move the plunger assembly 322 to the end 324 of the barrel 320, by pumping air into the space 340. See FIG. 8. This may be referred to as the home position. Air in the space 342 is transferred to the system 10, or at least to the tubing 308, 366.

Figure 8:
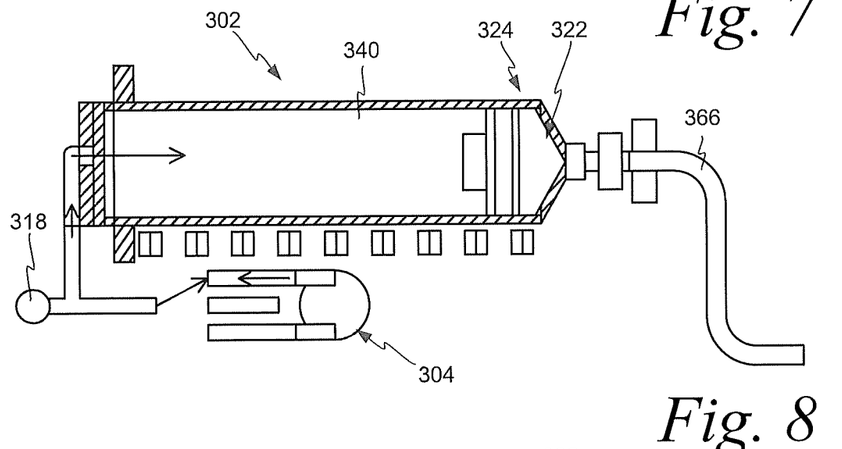
Figure 9:
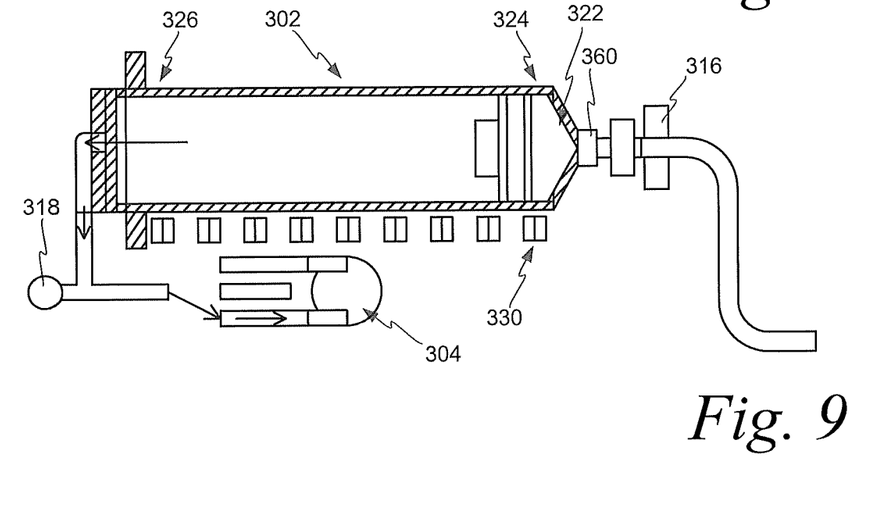
Figure 10:
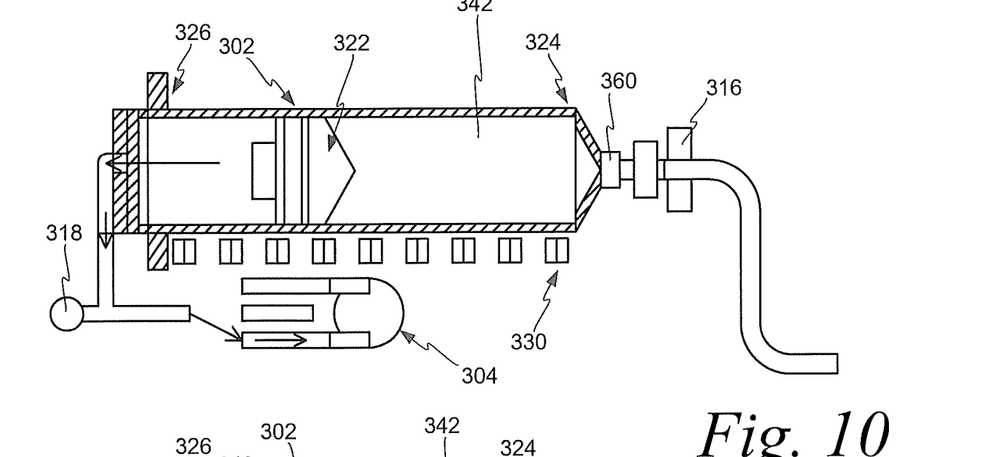
Figure 11:
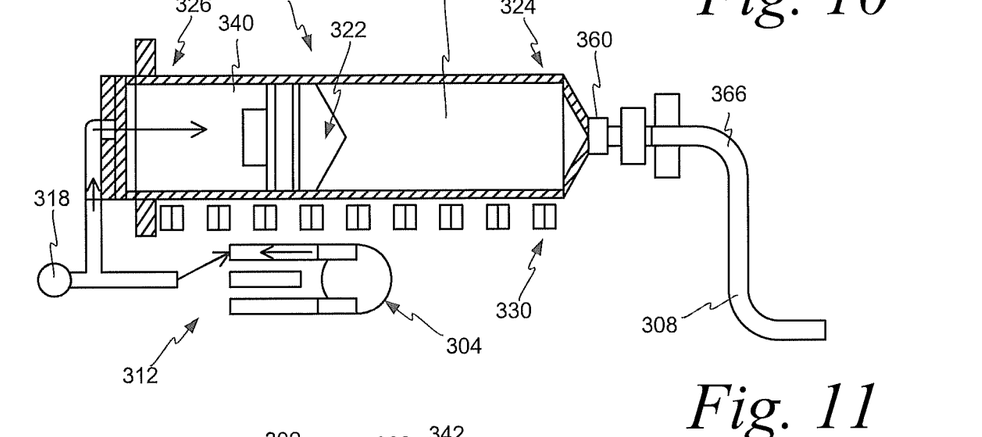
Figure 12:
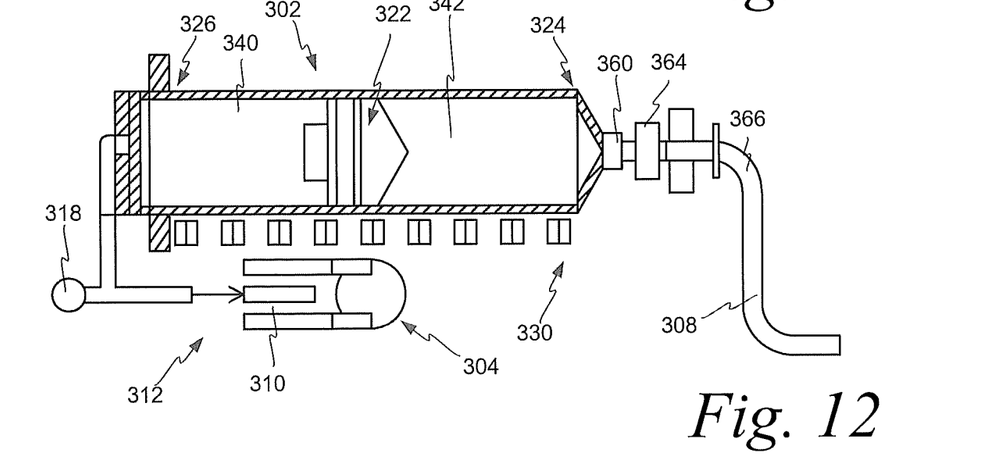
Figure 13:
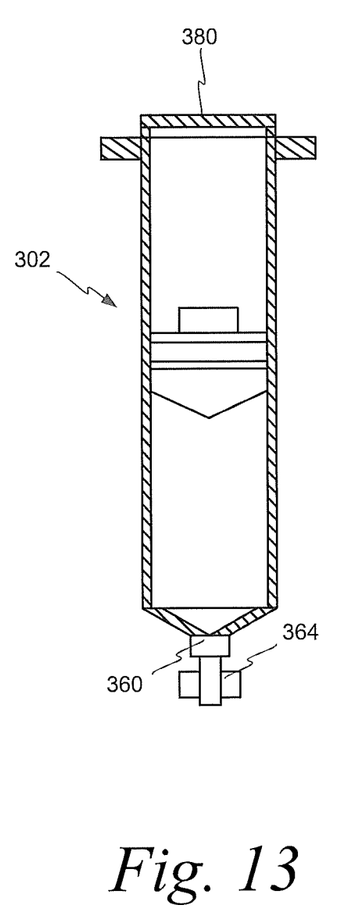
FIG. 13 is a cross-sectional view of a pre-filled syringe produced using the embodiment of FIG. 6.
Figure 14:
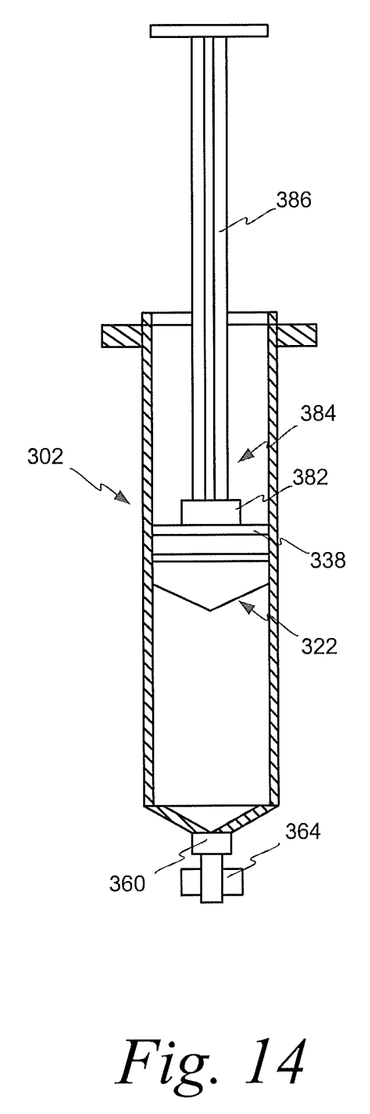
FIG. 14 is a cross-sectional view of the pre-filled syringe of FIG. 13 configured for administration to a patient.

The method then continues with the controller 314 operating the pump 304 to pull a vacuum (see FIG. 9), which causes the plunger head assembly 322 to move from the position (home position) illustrated in FIG. 8, where the plunger head assembly 322 is near the first end 324 to a position as is illustrated in FIG. 10, wherein the plunger head assembly 322 is nearer the second end 326. Initially, the movement of the plunger head assembly 322 may cause air to enter the space 342. The controller 314 may use the fluid sensor 316 to determine when the fluid enters the tip 360 of the syringe and the position detector 330 to determine the volume of air that will later need to be purged from the syringe 302. This volume may be referred to as the tare volume.

The method continues with the controller 314 operating the pump 304 to move the plunger head assembly 322 to draw a volume into the space 342 that may be equal to the desired volume of fluid from the container 150 that is to be filled into the syringe 302 (which may be referred to as the fill volume) and the volume of air initially drawn into the syringe 302 at the beginning of the method (i.e., the tare volume). The volume that is the sum of the fill volume and the tare volume may be referred to as the stop volume. See FIG. 10.

At this point, it may be desirable to remove the air that remains in the syringe 302. The syringe 302 may be oriented such that the tip 360 is vertical to allow the air to move in the direction of the tip 360. The controller 314 then operates the pump 304 to move the plunger head assembly 322 in the direction of the first end 324, thereby purging the air out of the space 342 into the line 366 in the direction of the system 10. See FIG. 11. The controller 314 determines when the fluid in the space 342 reaches the tip 360, and then ceases operation of the pump 304 and vents the space 340 via the valve assembly 312 and the vent 310. See FIG. 12.

At this point, the syringe 302 is filled. The tubing 366 is heat sealed at the proximal end of the tubing 366, and the remainder of the tubing 366 is removed. The female luer-lock 364 remains connected to the tip 360 to cap the tip 360. The filter assembly 352 is removed from the syringe 302 by unscrewing the filter assembly 352 from the threaded aperture 350 at the second end 326 of the syringe 302. A closed cap 380 is screwed into the threaded aperture 350 to complete the final assembly. See FIG. 13. The luer-lock 364 and the cap 380 are intended to remain in place during shipment and/or storage to preserve the sterile condition of the fluid. The syringe 302 may then be subjected to additional processes, such as freezing.

At the time of use, the syringe 302 is prepared for use, for example by thawing the syringe 302 (where necessary) and by removing the closed cap 380. The disc 338 that is part of the plunger head assembly 322 has a threaded connection hub 382. A threaded first end 384 of a plunger handle 386 is screwed into the threaded connection hub 382, and the syringe 302 is ready for administration once the female luer-lock/cap 364 is removed. See FIG. 14.

As will be recognized, while the syringe pump 300 has been described as used in conjunction with the system 10, in place of the container 24 and connected to the outlet 66, it is possible to replace the syringe 28 and syringe pump 36 with the syringe pump 300. The operation of the syringe pump 300 may be generally as described above relative to system 10 with respect to syringe 28 and pump 36, except that one instance of the syringe 302 of the syringe pump 300 may be filled directly from the fluid pathway 62, and then removed from the syringe pump 300 and replaced with another instance of the syringe 302. The process of filling, removing, and replacing specific instances of the syringe 302 may then be repeated until all of the cell product has been transferred from the system 10. It may even be the case that the first syringe 302, which is used mainly in the early processing steps of the system 10 may be discarded prior to filling the instances of the syringe 302 with cell product from the spinning membrane separator 16.

In keeping with the disclosure, a method is provided for controlling the output flow rate of the pneumatic syringe pumping apparatus described above. The method controls several distinct phases of the process: break pressure targeting, glide control and vent control, and the method is the same regardless of whether a positive pressure or a vacuum is applied to the piston of the syringe.

Preferably, a proportional-integral-derivative ("PID") feedback loop is used for controlling the movement of the piston in the syringe. As is well known in the art, such a feedback loop continuously calculates an error value as the difference between a desired set point and a measured process variable, and applies a correction based on proportional, integral, and derivative terms. The overall control function can be expressed mathematically as:

$$u(t) = K_p e(t) + K_i \int_0^t e(t')dt' + K_d \frac{de(t)}{dt};$$

where u(t) is the output of the controller, e is the error, t is the current time, and $K_p$, $K_i$, and $K_d$ are coefficients that describe the relative strength of the control due to that element.

Figure 15:
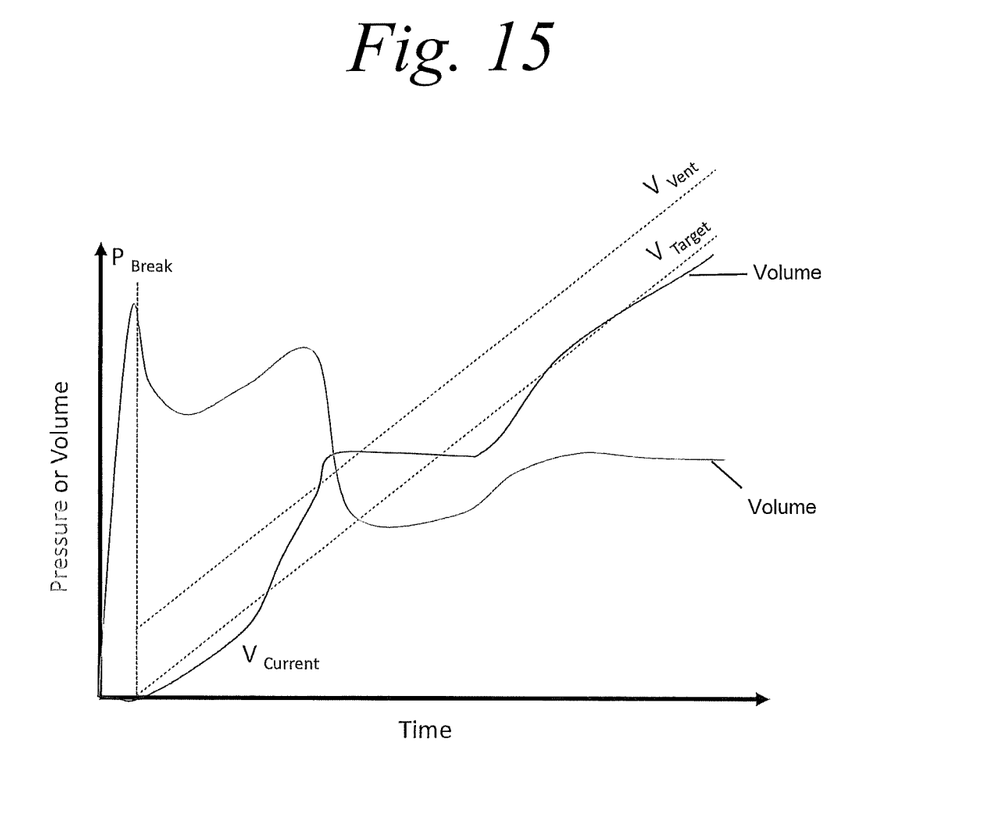
FIG. 15 is a representative plot of Pressure (i.e., the pressure exerted on the piston) or Volume (the volume of fluid moved by the piston) vs. Time for one cycle of movement of a piston within a syringe is illustrated.

With reference to FIG. 15, a representative plot of Pressure (i.e., the pressure exerted on the piston) or Volume (the volume of fluid moved by the piston) vs. Time for one cycle of movement of a piston within a syringe is illustrated. FIGS. 16-19 are similar to FIG. 15, except that the time interval for each of the distinct phases of the process is highlighted. Specifically, in FIG. 16, the break pressure targeting phase is highlighted; in FIG. 17, the glide control phase is highlighted; in FIG. 18, the vent control phase is highlighted; and in FIG. 19, a phase in which the controls are restarted is highlighted.

Figure 16:
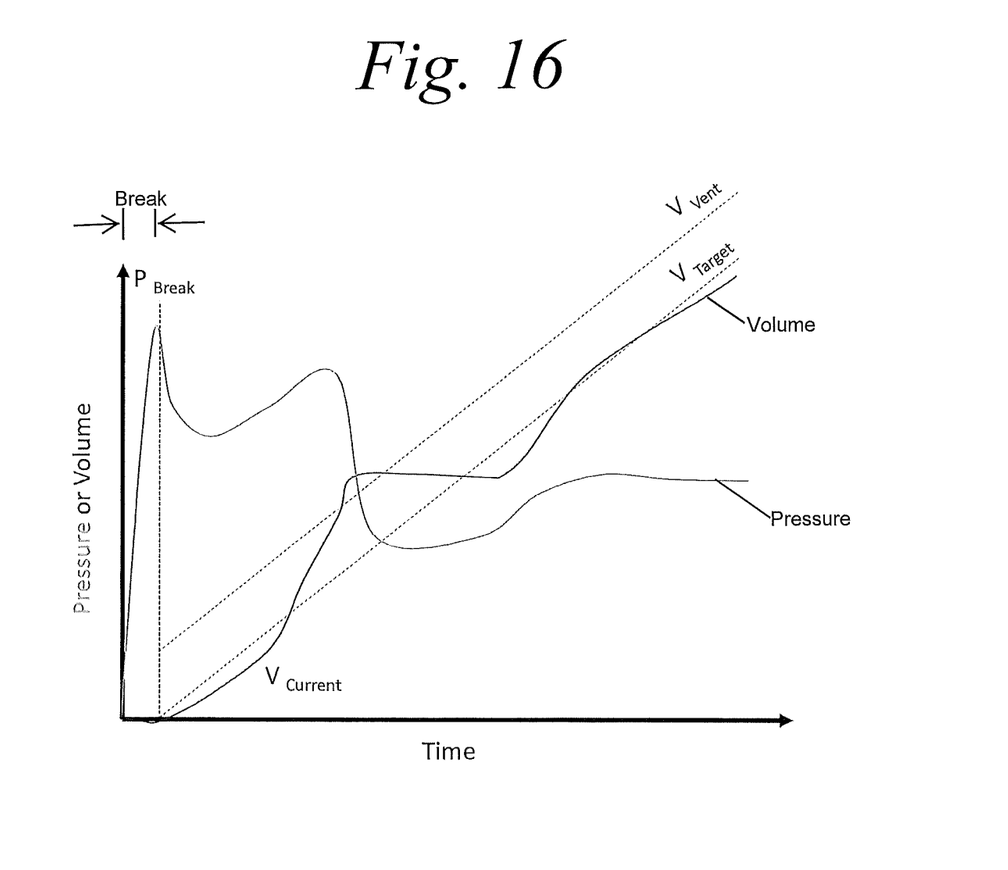
FIG. 16 is similar to FIG. 15, except that the break pressure targeting phase is highlighted.

In the break pressure targeting phase highlighted in FIG. 16, pressure is applied by the pump to the piston (starting at time=-0-), and increased up to the point where the pressure will overcome the friction between the piston and the syringe to start to move the piston. In this phase, the system uses proportional control (P-control) to target a pre-determined break pressure, as defined for a nominal disposable syringe component. Preferably, the break pressure will be empirically characterized by sampling a wide variety of syringes, and be set on the low end of the distribution such that, in most cases, the system will reach the minimum break pressure before movement of the piston is detected. When this initial set point has been reached, the controller will increase the set point until movement of the piston is detected.

At time t=-0-, the air pump turns and generates pressure at a high rate. As the current pressure approaches the break pressure, the pump rate is decreased linearly (to zero) until the break pressure is reached. If the system has reached the break pressure without detecting piston movement, the target pressure will be slowly increased.

Figure 17:
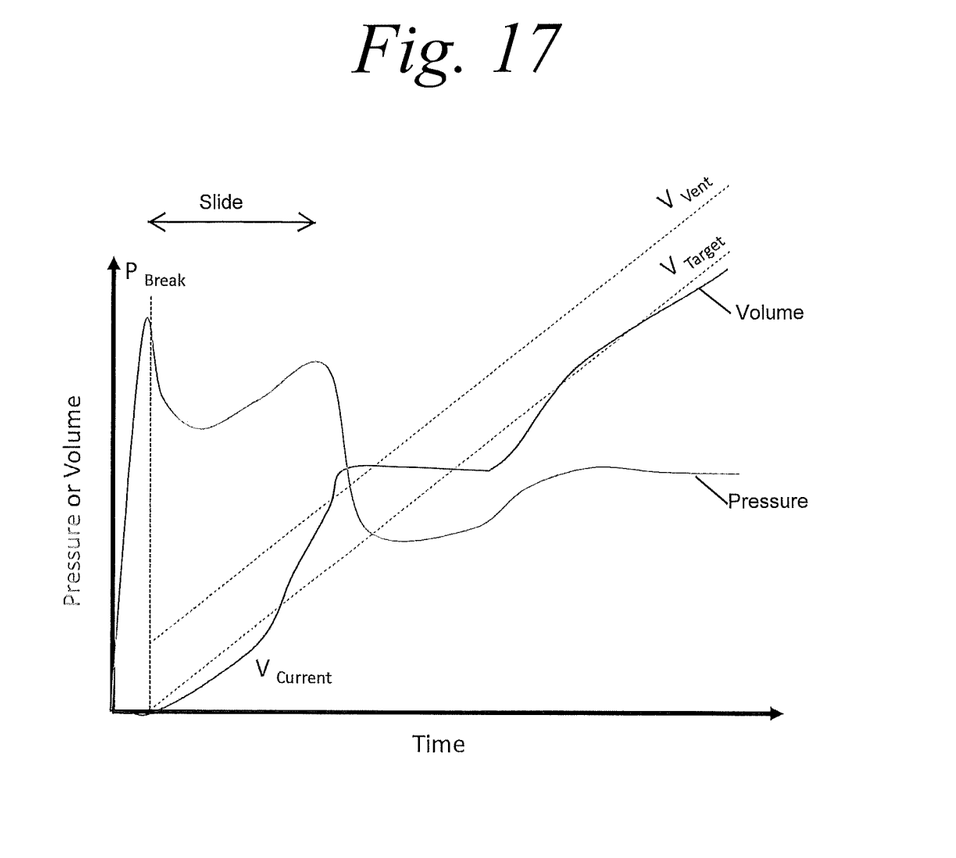
FIG. 17 is similar to FIG. 15, except that the glide control phase is highlighted.

Once piston movement is detected, the pump will enter the glide control phase, as highlighted in FIG. 17. When movement of the piston is detected, the target volume ($V_{target}$) is incremented, according to the desired flow rate. Proportional-Integral controls (PI control) are used to modulate the air pump speed based off the volumetric error ($V_{error}=V_{target}-V_{current}$). When the current volume is lower than the target volume, the air pump rate is increased to push the piston faster. When the current volume is higher than the target volume, the air pump stops and pressure is maintained in an attempt to keep the piston gliding at the desired rate. Controlling the volumetric error results in targeting a constant flow rate, whereas attempts to directly control the flow rate through a liner regression of the current volume requires time to elapse and, thus, decreases the ability to control the flow rate over a short time interval.

Figure 18:
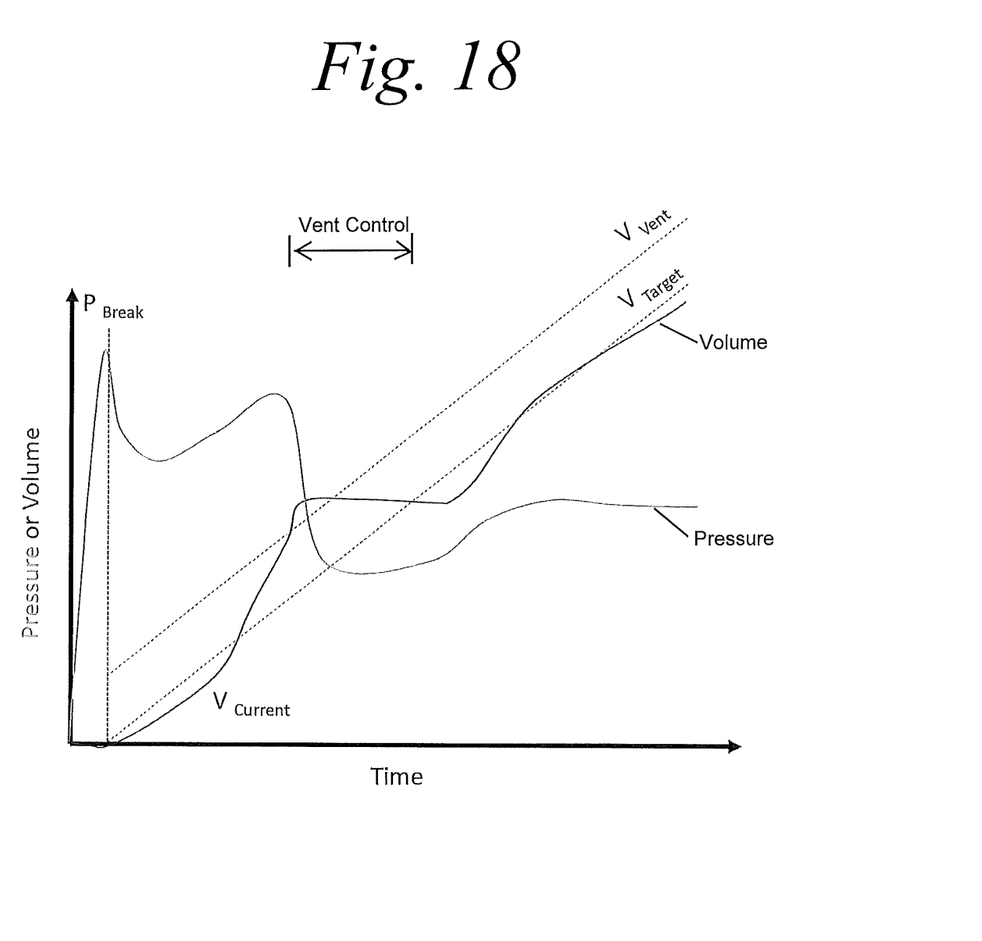
FIG. 18 is similar to FIG. 15, except that the vent control phase is highlighted.

With reference to FIG. 18, the vent control phase is highlighted. For the vent control, a vent volume limit ($V_{vent}$) is set for each target volume (as indicated by the line labeled $V_{vent}$ in FIGS. 15-19). The vent volume limit is a predetermined multiple of the target volume (as indicated by the line labeled $V_{vent}$ being parallel to the line labeled $V_{target}$) and may be determined empirically. If the current volume ($V_{current}$) exceeds the vent volume, the syringe pressure is released in a controlled-duration vent to atmosphere. The venting should quickly slow the rate of travel of the piston (perhaps to a stop), and allow time for the target volume to catch up to the current volume as time elapses. The vent duration may be constant or variable, and derived by the magnitude of the volumetric error. A venting operation may also be triggered by background systems that monitor the short-duration slope-regression of the current volume (flow rate) and/or the slope-regression of the volumetric error.

Figure 19:
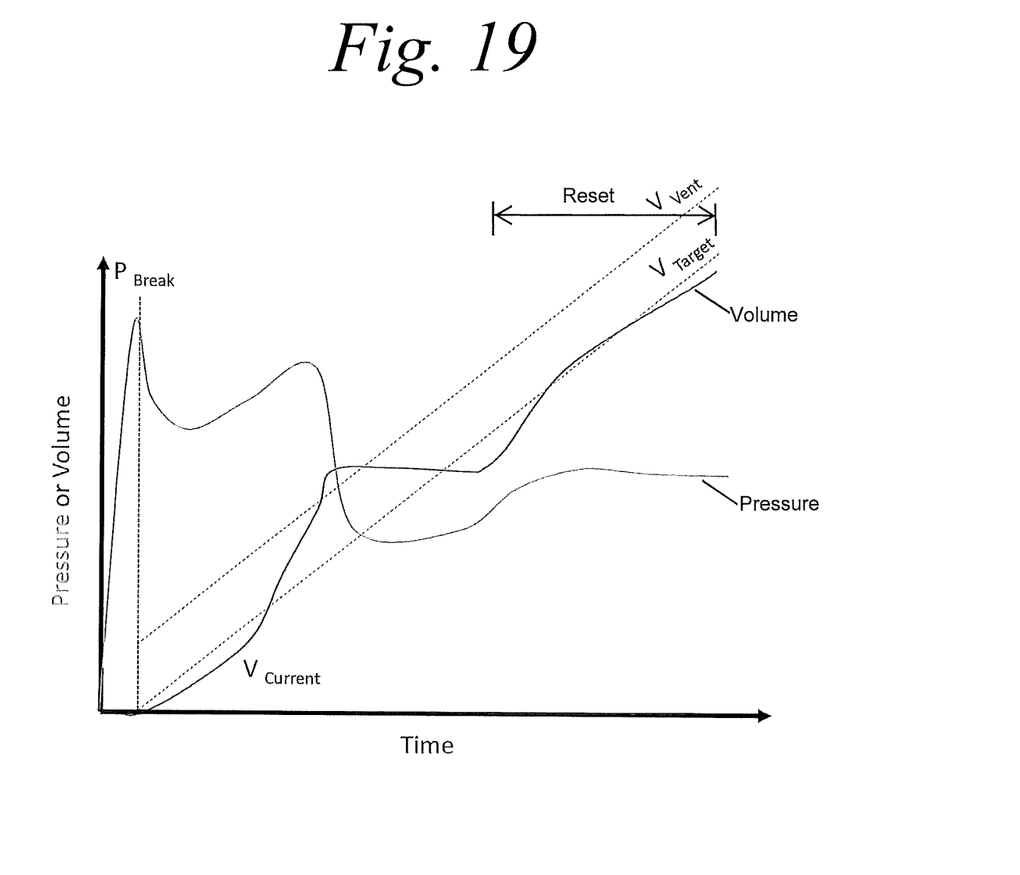
FIG. 19 is similar to FIG. 15, except that a phase in which the controls are restarted is highlighted.

FIG. 19 highlights a phase in which the controls are reset in response to the system detecting that the piston has stopped moving, regardless of whether the cause is a venting operation, active control to stop movement of the piston, or the inherent resistance between the piston and the syringe barrel. Under such circumstances, the system will enter the break pressure targeting phase (FIG. 16), followed by the glide control phase (FIG. 17) without resetting the target volume. However, the target volume is reset if the target flow rate has been changed. Changing the flow rate by active control will often result in skipping the break pressure targeting phase, as the piston may already be in motion.

Thus, an improved method and system for processing small volumes of biological cells has been disclosed, in conjunction with an improved method and system for filling low-volume containers with the small volumes of processed. The description provided above, and the other aspects provided below, are intended for illustrative purposes, and are not intended to limit the scope of the disclosure to any particular method, system, apparatus or device described herein.

The invention claimed is:

1. A method for controlling movement of a piston having a first and second side in a syringe with a system comprising a pump for introducing pressurized air/vacuum into the syringe to act on the first side of the piston, the method comprising:
   a) operating the pump at a first speed introduce pressurized air/vacuum into the syringe to act on the first side of the piston;
   b) decreasing the speed of the pump linearly to -0- until a nominal break pressure is achieved;
   c) increasing the pump speed until movement of the piston is detected;
   d) determining a target volume $V_{target}$ for the syringe for each increment of time after movement of the piston has been detected based on a target flow rate;
   e) measuring a current volume $V_{current}$ of the syringe at each time increment;
   f) determining a volumetric error $V_{error}$ at each increment of time, such that $V_{error}=V_{target}-V_{current}$;
   g) determining a controller output based on $V_{error}$ using Proportional-Integral-Derivative control logic;
   h) adjusting the pump speed according to the controller output;
   i) establishing a vent volume $V_{vent}$ as a multiple of $V_{target}$ for each time increment;

j) at each increment of time, if $V_{current} > V_{vent}$, releasing pressure/vacuum from the first side of the piston until $V_{current} \leq V_{vent}$; and k) if movement of the piston has stopped, returning to step a) without resetting $V_{target}$.

2. The method of claim 1 wherein if $V_{error} < -0-$, increasing the pump speed, and if $V_{error} > -0-$, stopping the pump.

3. The method of claim 1 wherein the time duration for releasing the pressure/vacuum in step j) is constant.

4. The method of claim 1 further comprising resetting the target flow rate and resetting $V_{target}$ for the syringe for each increment of time after movement of the piston has been detected based on the reset target flow rate.

5. The method of claim 1 further comprising determining the nominal break pressure empirically for multiple syringes and is set so that the nominal break pressure is obtained before movement of the piston is detected.

6. The method of claim 1 wherein once the pump is operated at the first speed, the speed of the pump is decreased linearly to -0-.

7. The method of claim 1 wherein the time duration for releasing the pressure/vacuum in step j) is variable.

8. The method of claim 7 wherein the time duration for releasing the pressure/vacuum in step j) is a function of the magnitude of $V_{error}$.

9. A system for controlling movement of a piston having a first side and a second side in a syringe with air pressure/vacuum comprising:

a) a pump for introducing pressurized air/vacuum into the syringe to act on the first side of the piston, b) a sensor for determining the pressure/vacuum acting on the first side of the piston, c) a vent for selectively releasing the pressurized air vacuum acting on the first side of the piston, d) sensors for determining a location of the piston within the syringe and a volume of a space defined by syringe and the second side of the piston, and e) a controller configured to operate the system to perform the method of any of claims 1-8.

* * * * *